United States Patent [19]

Gravely et al.

[11] Patent Number: 4,476,881

[45] Date of Patent: Oct. 16, 1984

[54] MICROBIAL DIGESTION OF TOBACCO MATERIALS USING MIXED CULTURES

[75] Inventors: Lawrence E. Gravely, Louisville, Ky.; Vernon L. Geiss, Georgetown, Ind.

[73] Assignee: Brown & Williamson Tobacco Corporation, Louisville, Ky.

[21] Appl. No.: 493,121

[22] Filed: May 9, 1983

[51] Int. Cl.$^3$ ................... A24B 15/20; A24B 15/24; A24B 15/28

[52] U.S. Cl. .................................. 131/308; 131/310; 131/297

[58] Field of Search ............... 131/290, 308, 310, 297

[56] References Cited

U.S. PATENT DOCUMENTS

| | | | |
|---|---|---|---|
| 4,135,521 | 1/1979 | Malen | 131/308 |
| 4,308,877 | 1/1982 | Mattina | 131/308 |
| 4,407,307 | 10/1983 | Gaisch | 131/308 |

Primary Examiner—Vincent Millin
Attorney, Agent, or Firm—Charles G. Lamb

[57] ABSTRACT

A mixed complementary culture of bacteria and fungi are used to degrade pectin and cellulose components of tobacco materials.

8 Claims, No Drawings

MICROBIAL DIGESTION OF TOBACCO MATERIALS USING MIXED CULTURES

BACKGROUND OF THE INVENTION

This invention relates to a process for the treatment of tobacco. More particularly, this invention relates to a aprocess for treating tobacco stems with a mixed culture of bacteria and fungi for the degradation of pectin and cellulose in tobacco.

In the processing of tobacco for use in the manufacture of smoking producs, many times it is desired to treat the tobacco to remove undesirable components therein. In tobacco processing, various parts of the tobacco plants, such as lamina, veins, ribs and/or stems, although useful, are not necessarily in the proper size for incorporation into tobacco products. Because of their rigid cellular nature, the stems, veins and ribs normally require considerable mechanical work to provide a usuable tobacco product. To treat tobacco to break down the pectin or cellulose, which holds these plant segments together, microbial digestion has been proposed in the prior art. For example, U.S. Pat. No. 3,747,608 teaches the use of a pure culture of *Erwinia carotavora* to degrade the pectin binder in tobacco.

U.S. Pat. No. 3,513,857 teaches a tobacco stem treatment using polysaccharide-hydrolyzing enzymes exhibiting catalytic pectinase, cellulase and hemicellulase. U.S. Pat. No. 3,242,214 also teaches treatment of tobacco stems with water in a catalytic enzyme system wherein the system includes cellulase, hemicellulase and pectinase. U.S. Pat. No. 3,132,651 teaches the treating of tobacco in an aqueous mixture with cellulase from Aspergillus fungal species and then further treating with cellulase and proteolytic enzymes.

SUMMARY OF THE INVENTION

It is an object of the present invention to provide a process for simultaneous degradation of pectin and cellulose components of tobacco materials. It is another object of this invention to provide a process for the preparation of a mixed culture of bacteria and fungi for use in the treatment of tobacco materials. Other objects and advantages of this invention will become apparent to those skilled in the art upon consideration of the accompanying disclosure.

The present invention resides in the recognition that certain microorganisms in an aqueous solution, when coming in contact with tobacco, degrade the pectin fraction of tobacco materials while other microorganisms degrade the cellulose fraction of tobacco materials. It has been found that using a mixed culture of bacteria and fungi unexpectedly produces a better disintegration of the pectin fraction and cellulose fraction of tobacco materials than when the cultures are used separately or sequentially.

The preferred culture that has been found to produce enzymes for degradation of the pectin fraction of tobacco is *Erwinia carotovora* and a preferred enzyme producing microorganism that degrades the cellulose fraction of tobacco materials is *Trichoderma longibrachiatum*. A mixed culture containing the aforementioned enzymes has been found to be particularly applicable for use in reconstituted tobacco production processes; the resulting product being a tobacco material that is softer and more amenable to further treatment. Also, using the growing cultures in a tobacco treatment system provides the advantage of avoiding the separation step necessary in obtaining pure enzymes for addition to the tobacco treatment system. Furthermore, with living cultures, enzymes continue to be produced during treatment rather than requiring external replenishment. Even further, use of pure enzymes also often limits the pH range for functioning more than when using cultures themselves. Therefore, pH control of tobacco digestion using mixed cultures is not as critical for successful tobacco treatment as is necessary when using pure enzymes.

DESCRIPTION OF THE PREFERRED EMBODIMENT

According to the present invention, one preferred method for treating tobacco with a mixed culture of bacteria and fungi is to prepare separately an aqueous medium containing microorganisms (bacterium) which will degrade pectin and an aqueous medium containing microorganisms (fungi) which will degrade cellulose.

In the preparation of an aqueous medium on which the bacteria and fungi may grow, a nutrient agar (first) solution is prepared by adding a commercially available nutrient agar, such as tryptone glucose extract agar, to distilled water, the amount of agar generally being at least 5 grams per liter. This solution is then sterilized as tubed slants; that is, test tubes containing the nutrient agar solution are placed at an angle to provide a slanted surface upon cooling, following autoclaving for at least 15 minutes at 15 psig and at 121° C. The sterilized medium is then placed in a refrigerator for later use.

EXAMPLE 1

In one example in accordance with the present invention, mixed cultures of bacteria and fungi were prepared for digestion of tobacco.

The first culture, a bacterium, preferably *Erwinia carotovora*, an aerobe, is grown on slants at room temperature for about one day. The slants are then washed with sterile distilled water and the washings (inoculum) are then used to inoculate Nutrient Dextrose Broth (for example 7.5 ml inoculum added to 250 ml broth in a 500 ml flask).

The flasks were then incubated for 24 hours in a water bath shaker at 30° C. and rotated at 229 revolutions per minute.

A mixture of the resulting bacterial culture produced was then prepared as shown in Table 1.

TABLE 1

| Component | Volume (or weight) |
|---|---|
| 1. Bacterial Inoculum From Nutrient Dextrose Broth | 600 ml |
| 2. Burley Stem | 480 gram |
| 3. Tap Water | 600 ml |

The mixture was then incubated for 16 ours at ambient temperatures while being agitated at 600 rpm using an internal stirring shaft and blade and aeration at a rate of 9 liters per minute using an internal air ring.

After the incubation period, the culture had degraded the tobacco stem to a homogenous puree consistency. The tobacco stem puree containing the bacterial culture was then removed and used to treat additional stem. This first tobacco and culture growth step provided culture for additional tobacco treatments.

A second culture was prepared utilizing the Trichoderma culture (fungi), in the case *T. longibrachiatum*, where the second culture was grown for 20 days in cellulose medium in a rotary shaker at moderate speed and room temperature. The cellulose medium was prepared as described on page 392 published in American Chemical Society in *Cellulases and Their Applications,* Advances in Chemistry Series Vol 95, 1969. by M. Mandels & J. Weber.

The effect of the two cultures on tobacco stem was determined separately and in combination as shown in Table 2.

The treatment conditions were as follows: Water Vol. (ml.) 6,000; pH adjustment—none; treatment time—6 hours at a Temperature of 30° C.

TABLE 2

| Container | Culture Volume (ml) E. carotovora | Culture Volume (ml) T. longi brachiatum | Agitation Rate (rpm) | Aeration Rate ft³/min | Flue-cured/Burley Stem Mixture (Equal Parts) GMS. | Flue-cured/Burley Stem Mixture (Equal Parts) Slurry % Solids |
|---|---|---|---|---|---|---|
| A | 600 | 0 | 680 | 0.34 | 480 | 7.3 |
| B | 400 | 200 | 680 | 0.34 | 480 | 7.3 |
| C | 0 | 550 | 680 | 0.34 | 480 | 7.3 |

Cast sheets were made from the mixture by mixing 200 ml of treated slurry with 100 ml of tap water for one minute at low speed in a quart Waring blender jar and casting on a stainless steel plate over a steam bath.

The following observations, noted in Table 3, were made regarding hand cast sheets made from slurry from each container after six hours of treatment.

TABLE 3

| Sheet From Container: | Subjective Observations of Degree of Stem Breakup |
|---|---|
| A | Good, smooth sheet composed of many small fibers. Dark brown in color. |
| B | Very good, smooth sheet composed of many small fibers - fewer small fibers than sheet from "A" - lighter brown in color (closer to natural tobacco colors) than sheet from A. Back side of sheet has smoother finish than from A with fewer fibers on surface. |
| C | Would not cast into continuous sheet. |

PH readings of the Inoculum (pure cultures) are shown in Table 4 and the analyses of materials under mixed culture treatment are shown in Table 5.

TABLE 4

| Container | Inoculum Time (HRS) | pH |
|---|---|---|
| E. carotovora Inoculum (grown in burley stem and water mixture) used for Container "A" | 0 16 | 5.97 6.69 |
| T. longibrachiatum Inoculum Flask | 20 days | 4.83 |
| Uninoculated Flask | 20 days | 5.24 |

TABLE 5

| Container | Tobacco Treatments Time (HRS) | pH |
|---|---|---|
| "A" (E. carotovora Inoculated) | 0 | 6.07 |
| | 2 | 7.12 |
| | 4 | 7.06 |
| | 6 | 6.82 |
| "B" (Mixed Culture Inoculated - E. carotovora & T. longibrachiatum) | 0 | 5.74 |
| | 2 | 6.18 |
| | 4 | 6.95 |
| | 6 | 6.95 |
| "C" (T. longibrachiatum Inoculated) | 0 | 5.37 |
| | 2 | 5.41 |
| | 4 | 5.38 |
| | 6 | 5.39 |

The pH increased during treatment of stem with *E. carotovora* alone but remained constant when *T. longibrachiatum* was the only treatment organism. The mixed culture produced a pH pattern similar to the *E. carotovora* system. Ths pattern would not be contradictory to the combined action of the two cultures. In fact, this pH pattern, combined with the observed stem breakup, indicates that both cultures do function when mixed. The pH change is due to action of *E. carotovora* while *T. longibrachiatum* activity is evidenced by an improved digestion product compared to that of *E. carotovora* alone.

To demonstrate the effect of these two cultures, when mixed in sequence rather than simultaneously for tobacco digestion, the following experiment was conducted: *E. carotovora* culture as previously described was added to a tobacco stem mixture (flue-cured and burley) either with the mixture initially at its natural tobacco pH level (5.3-5.7) or with the pH initially adjusted upward to allow faster initial pectin degradation. With *E. carotovora* as the initial inoculum and in the first case the digestion of tobacco materials has been found to proceed slowly where the pH is initially unaltered compared to a state in which the pH is initially adjusted to approximately 6.0 *T. longibrachiatum* culture is added subsequent, in time, to addition of *E. carotovora* with the result that the total treatment will be improved in both instances as a result of the initial loosening of the tobacco fabric by *E. carotovora* at either initial pH.

The reverse addition of cultures, *T. longibrachiatum* first and *E. carotovora* second, has been found to have some effect on the tobacco but the effect is not as desirable as that accomplished where *E. carotovora* is presented first.

In another process within the scope of the present invention, the tobacco stems are presoaked for a selected time prior to being simultaneously treated by *E. carotovora* and *T. longibrachiatum* with the effect of decreasing the subsequent treatment time wherein the stems are exposed to the mixed cultures of bacteria and fungi.

Also within the scope of the present invention, other culture combinations of bacteria and fungi are possible in improving the quality of tobacco disintegration beyond that of using any one of the cultures alone.

Other pectolytic enzyme producing bacteria indicated to be effective include other Erwinia sp, *Bacillus polymyxa*, and Pseudomonas sp. In addition to *T. longibrachiatum*, other fungi indicated to be effective are those, such as, cellulase producing Aspergillus sp. and Penicillium sp.

What is claimed is:

1. A method for digestion of tobacco plant materials employing a mixed culture of bacteria and fungi which comprises:
    (i) mixing a selected quantity of water slurry of tobacco material with a selected quantity of pectolytic enzyme producing microorganisms and a selected quantity of a cellulase producing fungi;
(ii) aerating the mixture, and;
(iii) removing digested tobacco from the slurry.

2. The method of claim 1 wherien said pectolytic enzyme producing microorganisms are selected from the class consisting of Erwinia sp., Bacillus sp. and Pseudomonad sp.

3. The method of claim 1 wherein said cellulase producing fungi is selected from the class consisting of *Trichoderma longibrachiatum,* Asperigillus sp. and Penicillium sp.

4. The method of claim 1 wherien the pH of said slurry is adjusted to the range of 5.5 to 7.5 prior to addition of said mixed culture.

5. The method of claim 1 wherein the pectolytic enzyme producing bactarium is *Erwinia carotovora* and the cellulase producing fungi is *Trichoderma longibrachiatum.*

6. The method of claim 1 wherein the digestion is carried out at a temperature of about 30° C.

7. The method of claim 1 wherein the digestion is carried out at from about 5 to 7 hours.

8. The method of claim 1 wherein the digestion is carried out at a slurry solids content of about 7.3%.

* * * * *